United States Patent [19]

Wong

[11] Patent Number: 5,492,904
[45] Date of Patent: Feb. 20, 1996

[54] COMPOSITION OF ANGIOTENSIN-II RECEPTOR ANTAGONISTS AND CALCIUM CHANNEL BLOCKERS

[75] Inventor: Pancras C. B. Wong, Wilmington, Del.

[73] Assignee: E. I. du Pont de Nemours and Company, Wilmington, Del.

[21] Appl. No.: 281,724

[22] Filed: Jul. 28, 1994

Related U.S. Application Data

[63] Continuation-in-part of Ser. No. 938,800, Sep. 1, 1992, abandoned, which is a continuation-in-part of Ser. No. 700,740, May 15, 1991, abandoned.

[51] Int. Cl.⁶ .......................... A61K 31/55; A61K 31/41
[52] U.S. Cl. ..................... 514/211; 514/381; 514/929
[58] Field of Search ........................... 514/211, 381, 514/929

[56] References Cited

U.S. PATENT DOCUMENTS 4,983,598  1/1991  Caver et al. ........................ 514/211

OTHER PUBLICATIONS

CA 109(15):129008g, Carini et al., 1988.
CA 112(13):118817f, Carini et al., 1989.

*Primary Examiner*—Kimberly Jordan

[57] ABSTRACT

Novel pharmaceutical compositions containing a combination of an angiotensin-II antagonist and a calcium channel blocker such as 2-butyl-4 chloro-1-[2-(1-H-tetrazol-5-yl)biphenyl-4-yl)methyl]-5-(hydroxymethyl) imidazole, and diltiazem and the use of such compositions in the treatment of hypertension and congestive heart failure.

1 Claim, 1 Drawing Sheet

COMPOSITION OF ANGIOTENSIN-II RECEPTOR ANTAGONISTS AND CALCIUM CHANNEL BLOCKERS

CROSS REFERENCE TO RELATED APPLICATIONS

This application is a continuation-in-part of U.S. application Ser. No. 07/938,800, filed Sep. 1, 1992, now abandoned, which, in turn is a continuation-in-part of U.S. application Ser. No. 07/700,740, filed May 15, 1991 now abandoned.

SUMMARY OF THE INVENTION

This invention relates to novel pharmaceutical compositions containing an angiotensin-II receptor antagonist from a selected class in combination with a calcium channel blocker from a selected class useful for the treatment of hypertension and for the treatment of congestive heart failure.

BACKGROUND OF THE INVENTION

The selected class of angiotensin-II receptor antagonists and the selected class of calcium channel blockers essential as component parts of the novel compositions of this invention are compounds already known in the art as antihypertensive agents.

Angiotensin-II receptor antagonists useful in compositions of the invention are included in those compounds disclosed in published European Published application 0 324 377 the disclosure of which is incorporated herein by reference.

Calcium channel blockers useful in the compositions of this invention are selected from the group consisting of diltiazem, nifedipine, nitrendipine, nimodipine, niludipine, niguldipine, nicardipine, nisoldipine, amlodipine, felodipine, isradipine, ryosidine, verapamil, gallopamil and tiapamil.

DETAILED DESCRIPTION OF THE INVENTION

Figure 1:
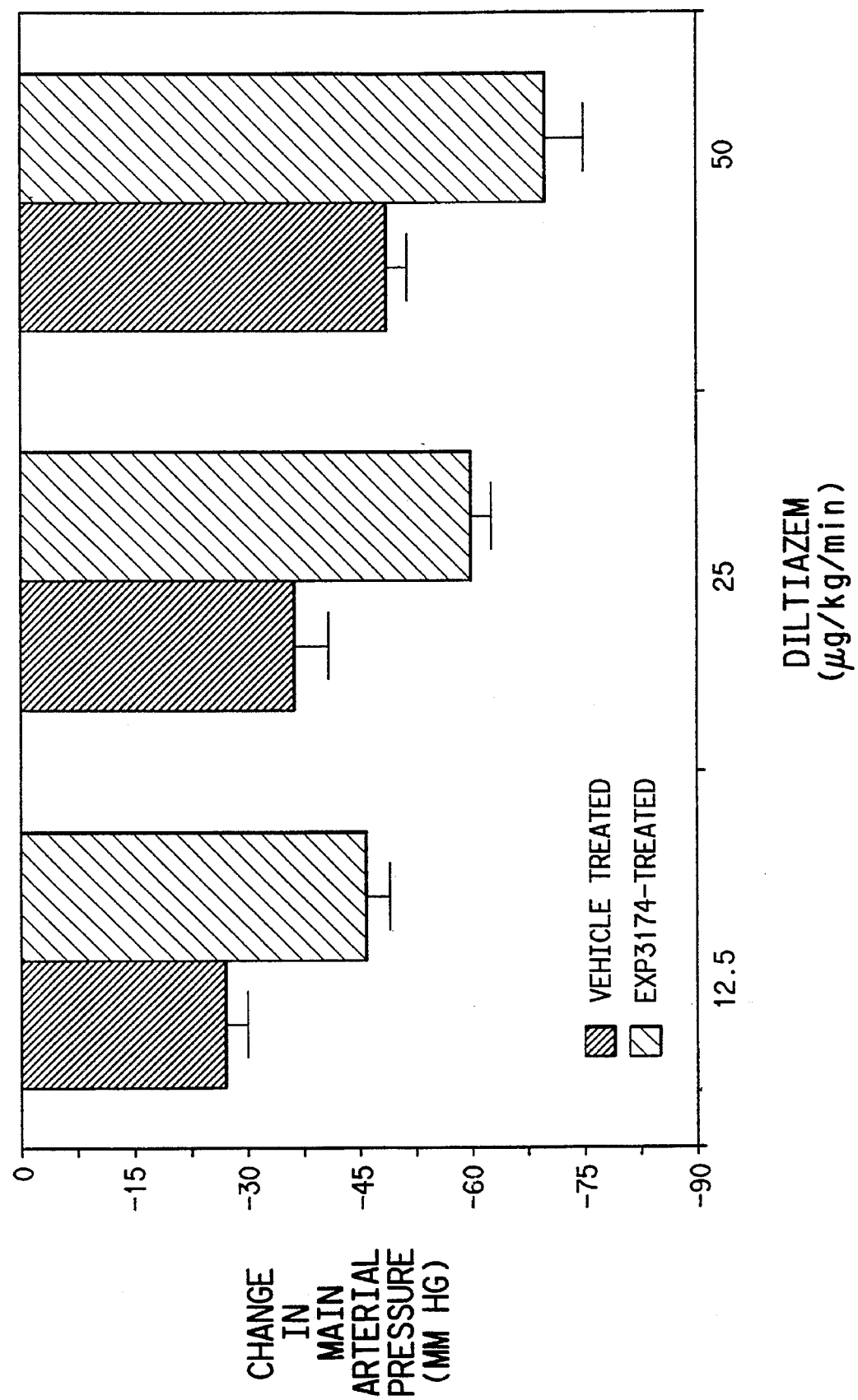
FIG. 1 shows antihypertensive results when an angiotensin-II receptor antagonist and diltiazem are administered individually and concomitantly.

The novel compositions of this invention contain a calcium channel blocker of the group defined above in combination with an angiotensin-II receptor antagonist compound of the following formula:

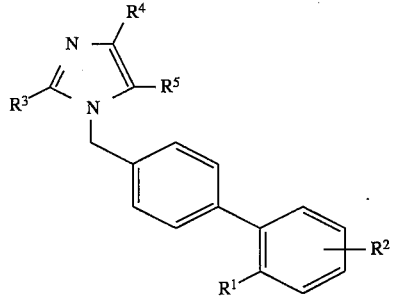

wherein
$R^1$ is $CO_2H$; $NHSO_2CF_3$ and

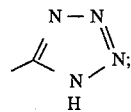

$R^2$ is H, alkyl of 1 to 4 carbon atoms, halogen, or alkoxy of 1 to 4 carbon atoms;

$R^3$ is alkyl, alkenyl or alkynyl of 3 to 7 carbon atoms;

$R^4$ is H, Cl, Br, I; alkyl of 1 to 4 carbon atoms; $C_vF_{2v+1}$, where v=1–3;

$R^5$ is $-(CH_2)_mOR^7$;

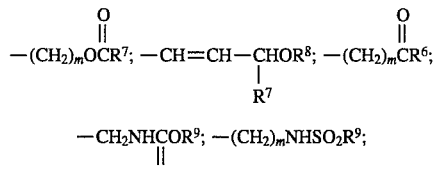

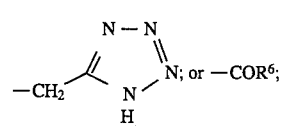

$R^6$ is H, alkyl of 1 to 5 carbon atoms or $OR^{10}$;

$R^7$ is H or alkyl of 1 to 4 carbon atoms;

$R^8$ is H, alkyl of 1 to 4 carbon atoms, or acyl of 1 to 4 carbon atoms;

$R^9$ is $CF_3$, alkyl of 1 to 6 carbon atoms or phenyl;

$R^{10}$ is H, alkyl of 1 to 6 carbon atoms, cycloalkyl of 3 to 6 carbon atoms, phenyl or benzyl;

m is 1 to 5 or a pharmaceutically acceptable salt thereof.

Preferred compounds of the above formula are those in which $R^1$ is

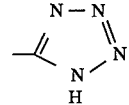

and $R^2$ is H. Illustrative compounds of this preferred scope are:

2-butyl-4-chloro-1-[(2'(1H-tetrazol-5-yl) biphenyl-4-yl)methyl]-5-(hydroxymethyl)imidazole 2-butyl-4-chloro-1-[(2'-(1H-tetrazol-5-yl) biphenyl-4-yl)methyl]imidazole-5-carboxylic acid 2 propyl-4-trifluoromethyl-1-[(2'-(1H-tetrazol-5-yl) biphenyl-4-yl)methyl]imidazole-5-carboxylic acid 2 propyl-4-chloro-1-[2'-(1H-tetrazol-5-yl) biphenyl-4-yl)methyl]imidazole-5-carboxaldehyde 2 propyl-4-ethyl-1-[(2'(1H-tetrazol-5-yl)biphenyl-4-yl)methyl]imidazole-5-carboxylic acid 2 propyl-4-ethyl-1-[(2'-1H-tetrazol-5-yl)biphenyl-4-yl)methyl]imidazole-5-carboxaldehyde 2-propyl-4-pentafluoroethyl-1-[(2'-(1H-tetrazol-5-yl) biphenyl-4-yl)methyl]imidazole-5-carboxylic acid 2-propyl-4-chloro-1-[2'-(1H-tetrazol-5-yl)biphenyl-4-yl)methyl]imidazole-5-carboxylic acid.

The potential antihypertensive effects of the combination of compounds of this invention may be demonstrated by administering the combination of active compounds to conscious spontaneously hypertensive rats. Rats received either orally or intravenously a dose of 0.1–30 mg/kg, preferably 0.1–10 mg/kg, of the desired calcium channel blocker, or a dose of 0.1–30 mg/kg, preferably 0.1–10 mg/kg, of the desired angiotensin-II receptor antagonist, or a combination of the two doses of the calcium channel blocker and the angiotensin-II receptor antagonist. Arterial blood pressure is continuously measured directly through a carotid artery catheter and recorded using a pressure transducer and a polygraph. Blood pressure levels after treatment are compared to pretreatment levels.

Example 1

As illustrative of the above, the antihypertensive effect of EXP3174, which is the compound 2-butyl-4-chloro-1-[(2'-(1H-tetrazol-5-yl)biphenyl-4-yl)methyl]imidazole-5-carboxylic acid, in combination with diltiazem was evaluated in anesthetized spontaneously hypertensive rats (SHR). Male SHR, 18–21 weeks old, were anesthetized with inactin (120 mg/kg i.p.) and then surgically prepared with arterial and venous catheters. The arterial catheter was connected to a Gould pressure transducer coupled to a Grass polygraph for monitoring arterial pressure. EXP3174 was dissolved in a mixture of 5% $NaHCO_3$ and 5% dextrose (50:50). Diltiazem was dissolved in saline. The following groups of experiments were carried out in anesthetized SHR.

After a stabilization period of 30 minutes, vehicle (for EXP3174) at 1 ml/kg i.v. or EXP3174 at 0.3 mg/kg i.v. was given. Thirty minutes later, vehicle (for diltiazem) at 0.2 ml/kg.min or diltiazem at 12.5, 25 or 50 µg/kg.min. was infused i.v. for 20 minutes. The change in mean arterial pressure at the end of the i.v. infusion from the pre-treatment mean arterial pressure was then determined.

Compared to the vehicle-treated group (n=8) EXP3174 at 0.3 mg/kg i.v. (n=8) did not change mean arterial pressure significantly. As shown in FIG. 1, diltiazem at 12.5 (n=5), 25 (n=5) and 50 (n=9) µg/kg.min i.v. significantly decreased mean arterial pressure by 27±3, 36±5, and 49±2 mm Hg, respectively. Surprisingly, EXP3174 at 0.3 mg/kg i.v. in combination with diltiazem at 12.5 (n=5), 25 (n=5) and 50 (n=8) µg/kg.min i.v. decreased mean arterial pressure further by 46±3, 60±2, and 70±6 mm Hg, respectively which were significantly different from the corresponding diltiazem-treated group. These results indicate that EXP3174 at a low dose of 0.3 mg/kg i.v. did not change mean arterial pressure significantly but unexpectedly enhanced the hypotensive effect of diltiazem at 12.5, 25, and 50 µg/kg.min i.v. by 70%, 67%, and 43%, respectively, in anesthetized SHR.

The combination of active compounds of this invention are unexpectedly useful in treating hypertension. They are also of value in the management of acute and chronic congestive heart failure. These combinations also be expected to be useful in the treatment of secondary hyperaldosteronism, primary and secondary pulmonary hyperaldosteronism, primary and secondary pulmonary hypertension, renal failure such as diabetic nephropathy, glomerulonephritis, scleroderma, glomerular sclerosis, proteinuria of primary renal disease, end stage renal disease, renal transplant therapy, and the like, renal vascular hypertension, left ventricular dysfunction, diabetic retinopathy and in the management of vascular disorders such as migraine, Raynaud's disease, luminal hyperplasia, and to minimize the atherosclerotic process.

The combinations of this invention can be administered for the treatment of hypertension according to the invention by any means that effects contact of the active ingredient compounds with the site of action in the body of a warm-blooded animal in need of such treatment. For example, administration can be parenteral, i.e., subcutaneous, intravenous, intramuscular, or intra peritoneal. Alternatively, or concurrently, in some cases administration can be by the oral route.

The combinations of compounds can be administered by any conventional means available for use in conjunction with pharmaceuticals, either as individual therapeutic agents or in a combination with additional therapeutic agents. For example the combination of this invention of an angiotensin-II antagonist and calcium channel blocker can be combined with other antihypertensives and/or diuretics and/or angiotensin converting enzyme inhibitors such as amiloride, atenolol, bendroflumethiazide, chlorothalidone, chlorothiazide, clonidine, cryptenamine acetates and cryptenamine tannates, deserpidine, diazoxide, guanethidene sulfate, hydralazine hydrochloride, hydrochlorothiazide, metolazone, metoprolol tartate, methyclothiazide, methyldopa, methyldopate hydrochloride, minoxidil, pargyline hydrochloride, polythiazide, prazosin, propranolol, rauwolfia serpentina, rescinnamine, reserpine, sodium nitroprusside, spironolactone, timolol maleate, trichlormethiazide, trimethophan camsylate, benzthiazide, quinethazone, ticrynafan, triamterene, acetazolamide, aminophylline, cyclothiazide, ethacrynic acid, furosemide, merethoxylline procaine, sodium ethacrynate, captopril, delapril hydrochloride, enalapril, enalaprilat, fosinopril sodium, lisinopril, pentopril, quinapril hydrochloride, ramapril, teprotide, zofenopril calcium, diflusinal and the like.

The combinations of active compounds can be administered alone, but are generally administered with a pharmaceutical carrier selected on the basis of the chosen route of administration and standard pharmaceutical practice.

For the purpose of this disclosure, a warm-blooded animal is a member of the animal kingdom possessed of a homeostatic mechanism and includes mammals and birds.

Pharmaceutical compositions of the invention may contain from 10 to 300 mg of the desired calcium channel blocker and 1 to 100 mg of the angiotensin-II receptor antagonist per unit dose one or more times daily.

The active ingredients can be administered orally in solid dosage forms, such as capsules, tablets, and powders, or in liquid dosage forms, such as elixirs syrups, and suspensions. They can also be administered parenterally, in sterile liquid dosage forms.

Gelatin capsules contain the active ingredients and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

Useful pharmaceutical dosage-forms for administration of the compounds of this invention can be illustrated as follows:

Capsules

A large number of unit capsules are prepared by filling standard two-piece hard gelatin capsules each as with 100 milligrams of powdered active ingredients, 150 milligrams of lactose, 50 milligrams of cellulose, and 6 milligrams magnesium stearate.

Soft Gelatin Capsules

A mixture of active ingredients in a digestible oil such as soybean oil, cottonseed oil or olive oil is combinations prepared and injected by means of a positive displacement pump into gelatin to form soft gelatin capsules containing 100 milligrams of the active ingredients. The capsules are washed and dried.

Tablets

A large number of tablets are prepared by conventional procedures so that the dosage unit is 100 milligrams of active ingredients, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredients in 10% by volume propylene glycol. The solution is made to volume with water for injection and sterilized.

Suspension

An aqueous suspension is prepared for oral administration so that each 5 milliliters contain 100 milligrams of finely divided active ingredients, 100 milligrams of sodium carboxymethyl cellulose, 5 milligrams of sodium benzoate, 1.0 grams of sorbitol solution, U.S.P., and 0.025 milliliters of vanillin.

What is claimed is:

1. A method of treating hypertension which comprises administering to a patient in need of such treatment a therapeutically synergistic combination of a) 2-butyl-4-chloro-1-[(2'(1H-tetrazol-5-yl)biphenyl-4yl)methyl]imidazole-5-carboxylic acid or a pharmaceutically acceptable salt thereof and b) diltiazem to provide an amount of each of said component a) and component b) of said combination in a range of from 0.1 to 10 mg/kg.

* * * * *